(12) United States Patent
Xie et al.

(10) Patent No.: US 9,885,701 B2
(45) Date of Patent: Feb. 6, 2018

(54) METHOD FOR IMAGING BIOLOGIC FLUID SAMPLES USING A PREDETERMINED DISTRIBUTION

(71) Applicant: Abbott Point of Care, Inc., Princeton, NJ (US)

(72) Inventors: Min Xie, Plainsboro, NJ (US); Stephen C. Wardlaw, Lyme, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

(21) Appl. No.: 15/398,299

(22) Filed: Jan. 4, 2017

(65) Prior Publication Data

US 2017/0115271 A1   Apr. 27, 2017

Related U.S. Application Data

(63) Continuation of application No. 14/650,228, filed as application No. PCT/US2013/073636 on Dec. 6, 2013, now Pat. No. 9,576,180.

(60) Provisional application No. 61/896,432, filed on Oct. 28, 2013, provisional application No. 61/734,179, filed on Dec. 6, 2012.

(51) Int. Cl.
| | |
|---|---|
| *G01N 33/49* | (2006.01) |
| *G06K 9/00* | (2006.01) |
| *G01N 15/02* | (2006.01) |
| *G01N 15/14* | (2006.01) |
| *G01N 15/00* | (2006.01) |

(52) U.S. Cl.
CPC ......... *G01N 33/49* (2013.01); *G01N 15/0227* (2013.01); *G01N 15/1463* (2013.01); *G06K 9/0014* (2013.01); *G06K 9/00134* (2013.01); *G01N 2015/0065* (2013.01)

(58) Field of Classification Search
CPC .... G01N 33/49; G01N 15/02; G06K 9/00134; G06K 9/0014
USPC .......................................................... 356/39
See application file for complete search history.

(56) References Cited

U.S. PATENT DOCUMENTS

| | | | |
|---|---|---|---|
| 5,627,041 A * | 5/1997 | Shartle | ................... B01F 5/0604 422/50 |
| 6,350,613 B1 | 2/2002 | Wardlaw et al. | |
| 6,723,290 B1 | 4/2004 | Wardlaw | |
| 6,866,823 B2 * | 3/2005 | Wardlaw | ................ G01N 15/05 356/244 |

(Continued)

OTHER PUBLICATIONS

CN office action for CN201380066596.9 dated May 31, 2017.

*Primary Examiner* — Roy M Punnoose
(74) *Attorney, Agent, or Firm* — O'Shea Getz P.C.

(57) ABSTRACT

A method for analyzing a biologic fluid sample includes the steps of: a) providing a spatially mapped chamber; b) providing a predetermined repeatable non-uniform spatial distribution of one or more constituents within the sample, which distribution indicates the presence or absence of a statistically significant number of constituents within the sample in each chamber sub-region; c) selecting one or more image techniques for each sub-region based on the presence or absence of the statistically significant number of one or more constituents in that sub-region as indicated by the distribution; d) creating image data representative of the biologic fluid sample in each sub-region, using the one or more image techniques selected for that sub-region; and e) analyzing the sample.

18 Claims, 5 Drawing Sheets

(56) References Cited

U.S. PATENT DOCUMENTS

| | | | |
|---|---|---|---|
| 7,764,821 B2 | 1/2010 | Coumans et al. | |
| 7,731,901 B2 | 6/2010 | Wardlaw | |
| 7,850,916 B2 | 12/2010 | Wardlaw | |
| 8,326,008 B2 | 12/2012 | Lalpuria et al. | |
| 8,472,693 B2 | 6/2013 | Davis et al. | |
| 8,786,694 B2 | 7/2014 | Xie et al. | |
| 8,797,527 B2 * | 8/2014 | Hukari | G01N 21/01 356/246 |
| 9,082,166 B2 | 7/2015 | Yu et al. | |
| 9,576,180 B2 * | 2/2017 | Xie | G01N 21/6458 |
| 2003/0180773 A1 | 9/2003 | Cohen et al. | |
| 2007/0087442 A1 | 4/2007 | Wardlaw | |
| 2009/0163785 A1 | 6/2009 | Nelson | |
| 2009/0298191 A1 | 12/2009 | Whitesides et al. | |
| 2010/0177189 A1 | 7/2010 | Rughani et al. | |
| 2011/0108422 A1 | 5/2011 | Heller et al. | |
| 2011/0157344 A1 | 6/2011 | Xie et al. | |
| 2011/0206557 A1 | 8/2011 | Blum et al. | |
| 2011/0244581 A1 | 10/2011 | Nikonorov et al. | |
| 2012/0034647 A1 | 2/2012 | Herzog et al. | |
| 2012/0155739 A1 | 6/2012 | Schlarb et al. | |
| 2012/0219457 A1 | 8/2012 | Verrant et al. | |
| 2012/0263369 A1 | 10/2012 | Xie et al. | |
| 2013/0169948 A1 | 7/2013 | Xie et al. | |

* cited by examiner

FIG. 8

METHOD FOR IMAGING BIOLOGIC FLUID SAMPLES USING A PREDETERMINED DISTRIBUTION

This application is a continuation of U.S. patent application Ser. No. 14/650,228 filed Jun. 5, 2015, which claims priority to PCT Patent Appln. No. PCT/US2013/073636 filed Dec. 6, 2013, which is entitled to the benefit of and incorporates by reference essential subject matter disclosed in the U.S. Patent Appln. No. 61/734,179, filed Dec. 6, 2012 and U.S. Patent Appln. No. 61/896,432 filed Oct. 28, 2013.

BACKGROUND OF THE INVENTION

1. Technical Field

The present invention generally relates to methods for imaging a biologic fluid sample, and more specifically relates to methods and apparatuses for imaging a biologic fluid sample at more than one resolution and in some instances less than the entire sample.

2. Background Information

Historically, biologic fluid samples such as whole blood, urine, cerebrospinal fluid, body cavity fluids, etc., have had their particulate or cellular contents evaluated by smearing a small undiluted amount of the fluid on a slide and evaluating that smear under a manually operated microscope. Reasonable results are attainable using these techniques, but they rely heavily upon the technician's experience and technique. These techniques are also labor-intensive and thus not practically feasible for commercial laboratory applications.

Automated apparatuses for analyzing biologic fluid samples are known, including some that are adapted to image a sample of biologic fluid quiescently residing within a chamber. Automated analysis devices can produce results that are as accurate as manual examination methods in a substantially reduced period of time. Nonetheless, the speed at which automated devices operate can be significantly limited by high resolution imaging. High resolution imaging produces substantial volumes of electronic data that must be processed by the apparatus. It would be desirable to provide an automated device and methodology that reduced the time required to consistently provide accurate results.

SUMMARY OF THE DISCLOSURE

According to an aspect of the present invention, a method for analyzing a biologic fluid sample is provided. The method includes the steps of: a) providing a chamber for holding the biologic fluid sample, which chamber is spatially mapped to divide the chamber into a plurality of sub-regions; b) providing a predetermined repeatable non-uniform spatial distribution of one or more constituents within the sample when the sample is disposed within the chamber, wherein the distribution indicates the presence or absence of a statistically significant number of at least one of the constituents within the sample in each sub-region of the chamber; c) disposing the biologic fluid sample within the chamber; d) selecting one or more image techniques for each sub-region based on the presence or absence of the statistically significant number of one or more constituents in that sub-region as indicated by the distribution; e) creating image data representative of the biologic fluid sample in each sub-region, using the one or more image techniques selected for that sub-region; and f) analyzing the sample, using the image data representative of the biologic fluid sample in each sub-region.

According to another aspect of the present invention an apparatus for imaging a biologic fluid sample is provided. The apparatus includes a chamber, a sample illuminator, at least one image dissector, and a processor. The chamber is operable to hold the biologic fluid sample. The chamber is spatially mapped to divide the chamber into a plurality of sub-regions. The image dissector is operable to produce image signals representative of the sample residing within the chamber. The processor is adapted to include a predetermined repeatable non-uniform spatial distribution of one or more constituents within the sample disposed within the chamber. The distribution indicates the presence or absence of a statistically significant number of at least one of the constituents within the sample in each sub-region of the chamber. The processor is further adapted to select one or more image techniques for each chamber sub-region based on the presence or absence of the statistically significant number of one or more constituents in that sub-region as indicated by the distribution. The processor is further adapted to communicate with the sample illuminator and the image dissector to create image data representative of the biologic fluid sample in select chamber sub-regions, using the one or more image techniques selected for each of the select chamber sub-regions.

The present method and advantages associated therewith will become apparent in light of the detailed description of the invention provided below, and as illustrated in the accompanying drawings.

BRIEF DESCRIPTION OF THE DRAWINGS

FIG. 8 is a diagrammatic illustration of a mapped analysis chamber, illustrating an example of the number of tile images captured in mapped chamber.

DETAILED DESCRIPTION OF THE INVENTION

Figure 1:
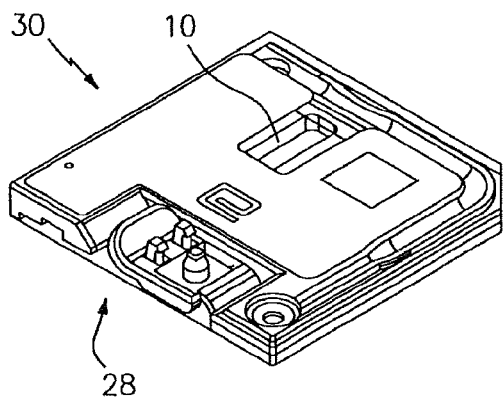
FIG. 1 is a perspective view of a biological fluid sample analysis cartridge.
Figure 5:
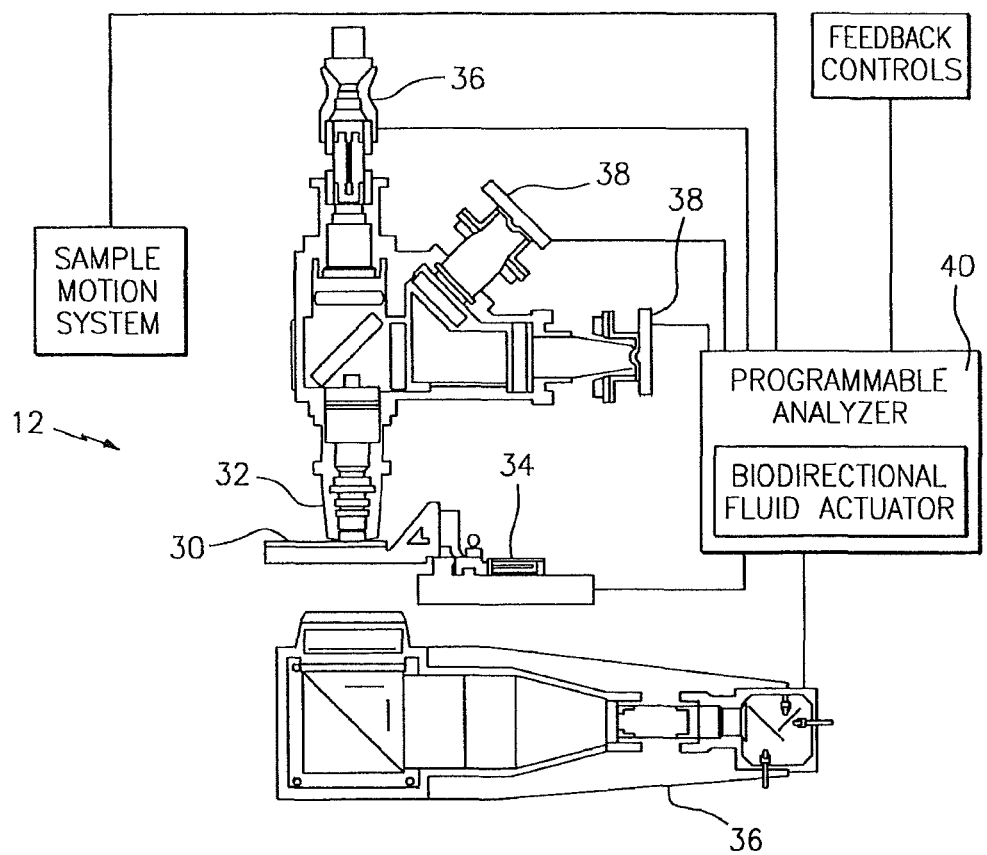
FIG. 5 is a diagrammatic view of an analysis device.

Referring to FIGS. 1 and 5, the present invention includes a method and an apparatus for an automated analysis of a biological fluid sample (e.g., whole blood) by an analysis device 12. The sample deposited in or disposed on a chamber 10 is imaged, and the image of the sample is analyzed using the analysis device 12.

Figure 2:
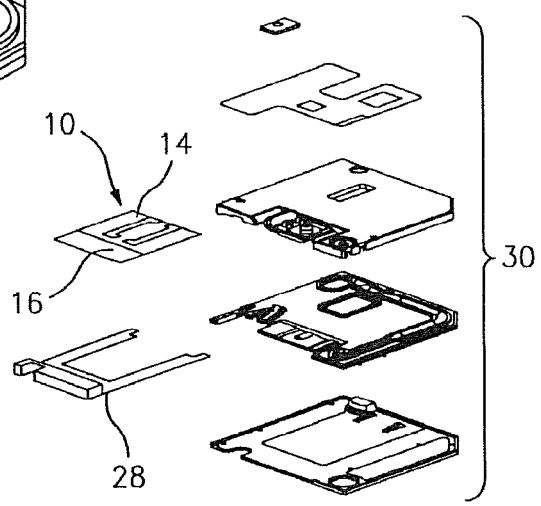
FIG. 2 is an exploded, perspective view of the biological fluid sample analysis cartridge shown in FIG. 1.
Figure 3:
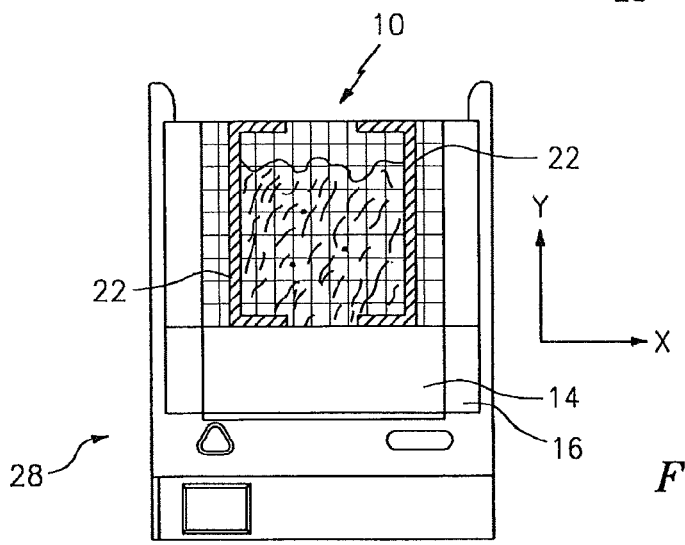
FIG. 3 is a planar view of a tray holding an analysis chamber.
Figure 4:
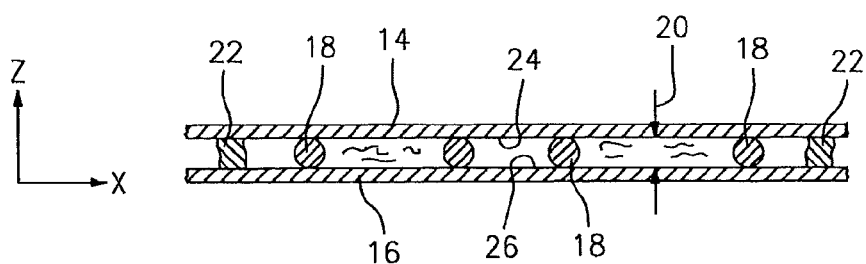
FIG. 4 is a sectional view of an analysis chamber.

An example of a chamber 10 that can be used with the present invention is shown in FIGS. 1-4. The chamber 10 is formed by a first planar member 14, a second planar member 16, and typically has at least three separators 18 disposed between the planar members 14,16. At least one of the planar members 14,16 is transparent. The height 20 of the chamber 10 is typically such that sample residing within the chamber 10 will travel laterally within the chamber 10 via capillary forces. FIG. 4 shows a cross-section of the chamber 10, including the height 18 of the chamber 10 (e.g., Z-axis).

FIG. 3 shows a top planar view of the chamber 10, illustrating the area of the chamber 10 (e.g., the X-Y plane). The lateral boundaries of the chamber 10 may be defined, for example, by glue lines 22 extending between the interior surfaces 24,26 of the planar members 14,16, or by lines of hydroscopic material disposed on a planar member surface that inhibit lateral travel there across. Sample may be introduced into the sample by engaging an inlet 21 formed between the planar members 14, 16 along an edge of the chamber (i.e., the "filling edge 23") with a bolus of sample. Upon contact with the filling edge 23, the sample is drawn into the chamber inlet by capillary force.

The present invention is not limited to use with any particular chamber embodiment. Examples of acceptable chambers are described in U.S. Pat. No. 7,850,916, and U.S. patent application Ser. Nos. 12/971,860; 13/341,618; and 13,594,439, each of which are incorporated herein by reference in its entirety. For purposes of this disclosure, the invention will be described as using the analysis chamber described in U.S. patent application Ser. No. 13/594,439. The analysis chamber 10 disclosed in the '439 Application is mounted on a tray 28 that is removable from a cartridge 30. FIG. 1 shows the cartridge 30 in assembled form. FIG. 2 shows an exploded view of the cartridge 30, including the analysis chamber 10 and the tray 28. FIG. 3 is a top view of the analysis chamber 10 mounted on the tray 28, depicting a sample residing within the chamber 10. FIG. 4 is a diagrammatic cross-section of the chamber 10. The analysis chamber 10 is typically sized to hold about 0.2 to 1.0 µl of sample, but the chamber 10 is not limited to any particular volume capacity, and the capacity can vary to suit the analysis application.

As indicated above, however, the present invention is not limited to use with the aforesaid chamber. An example of another "chamber" type of structure is a slide on which a sample may be smeared. To facilitate the description hereinafter, all such structures operable to hold a sample, and/or on which a sample may be deposited will be referred to hereinafter generically as a "chamber" and is not intended to be limited to the physical characteristics of any such structure unless specifically indicated.

The chamber 10 is operable to quiescently hold a liquid sample. The term "quiescent" is used to describe that the sample is deposited within the chamber 10 for analysis, and is not purposefully moved during the analysis. To the extent that motion is present within the blood sample, it will predominantly be due to Brownian motion of faulted constituents within the blood sample, which motion is not disabling of the use of this invention. A sample smear may be fixed onto a slide, with no appreciable movement of sample thereafter.

Referring to FIG. 5, an automated analysis device 12 is shown that controls, processes, images, and analyzes the sample disposed within the cartridge 10. U.S. Pat. No. 6,866,823 and U.S. patent application Ser. Nos. 13/077,476 and 13/204,415 (each of which is hereby incorporated by reference in its entirety) disclose examples of analysis devices 10 that have optics and a processor for controlling, processing, and analyzing images of the sample, which devices can be modified according to the present invention as will be described below. Except to the extent the analysis device is operable to perform the present methodology(ies), the present invention is not limited to any particular device. The analysis device 12 described below illustrates an example of a device that can be used.

The analysis device 12 includes optics including at least one objective lens 32, a cartridge positioner 34, a sample illuminator(s) 36, an image dissector 38, and a programmable analyzer 40. The positioner 34 is adapted to selectively change the relative positions of the objective lens 32 and the analysis chamber 10. One or both of the optics (e.g., the objective lens) and the analysis chamber 10 are moveable relative to the other along all relevant axes (e.g., X, Y, and Z). Relative movement of the chamber 10 in X-Y plane permits the optics to capture all fields of the sample residing within the chamber 10. Relative movement of the chamber 10 along the Z-axis permits change in the focal position of the optics relative to the sample height. The optics may include hardware that enables the analysis device 12 to capture one or more low resolution images of the sample residing within the chamber 10, as well as one or more high resolution images of the sample within the chamber 10. Acceptable optical hardware capable of taking both low and high resolution images of the sample include embodiments that have a plurality of objective lens (e.g., a high resolution objective lens and a low resolution objective lens) and embodiments wherein a single objective lens is used with one or more lenses that can be selectively moved into the optical path and are operable to change the resolution of the device. The present analysis device 12 is not limited to this exemplary optical hardware, however.

The sample illuminator 36 illuminates the sample using light at predetermined wavelengths. For example, the sample illuminator 36 can include an epi-fluorescence light source and a transmission light source. The transmission light source is operable to produce light at wavelengths associated with one or more of red, green, and blue light. The red light is typically produced in the range of about 600-700 nm, with red light at about 660 nm preferred. The green light is typically produced in the range of about 515-570 nm, with green light at about 540 nm preferred. The blue light is typically in the range of about 405-425 nm, with blue light at about 413 nm preferred. Light transmitted through the sample, or fluoresced from the sample, is captured using the image dissector, and a signal representative of the captured light is sent to the programmable analyzer, where it is processed into an image. The image is produced in a manner that permits the light transmittance or fluorescence intensity captured within the image to be determined on a per unit basis; e.g., "per unit basis" being an incremental unit of which the image of the sample can be dissected, such as a pixel.

An example of an acceptable image dissector 38 is a charge couple device (CCD) type image sensor that converts light passing through (or from) the sample into an electronic data format image. Complementary metal oxide semiconductor ("CMOS") type image sensors are another example of an image sensor that can be used. The signals from the image dissector 38 provide information for each pixel of the image, which information includes, or can be derived to include, intensity, wavelength, and optical density. Intensity values are assigned an arbitrary scale of, for example, 0 units to 4095 units ("IVUs"). Optical density ("OD") is a measure of the amount of light absorbed relative to the amount of light transmitted through a medium; e.g., the higher the "OD" value, the greater the amount of light absorbed during transmission. OD can be quantitatively described in optical density units ("ODU") or fractions thereof; e.g., a MilliODU is a $1/1000^{th}$ of an ODU. One "ODU" decreases light intensity by 90%. "ODU" or "MilliODU" as a quantitative value can be used for images acquired or derived by transmission light.

The programmable analyzer 40 includes a central processing unit (CPU) and is in communication with the cartridge positioner 34, sample illuminator 36, and image dissector 38. The programmable analyzer 40 is adapted (e.g., programmed) to send and receive signals from one or more of the cartridge positioner 34, the sample illuminator 36, and an image dissector 38. For example, the analyzer 40 is adapted to: 1) send and receive signals from the cartridge positioner 34 to position the cartridge 30 and chamber 10 relative to one or more of the optics, illuminator, and image dissector; 2) send signals to the sample illuminator 36 to produce light at defined wavelengths (or alternatively at multiple wavelengths); and 3) send and receive signals from the image dissector 38 to capture light for defined periods of time. It should be noted that the functionality of the programmable analyzer may be implemented using hardware, software, firmware, or a combination thereof. A person skilled in the art would be able to program the processing unit to perform the functionality described herein without undue experimentation.

Figure 6:
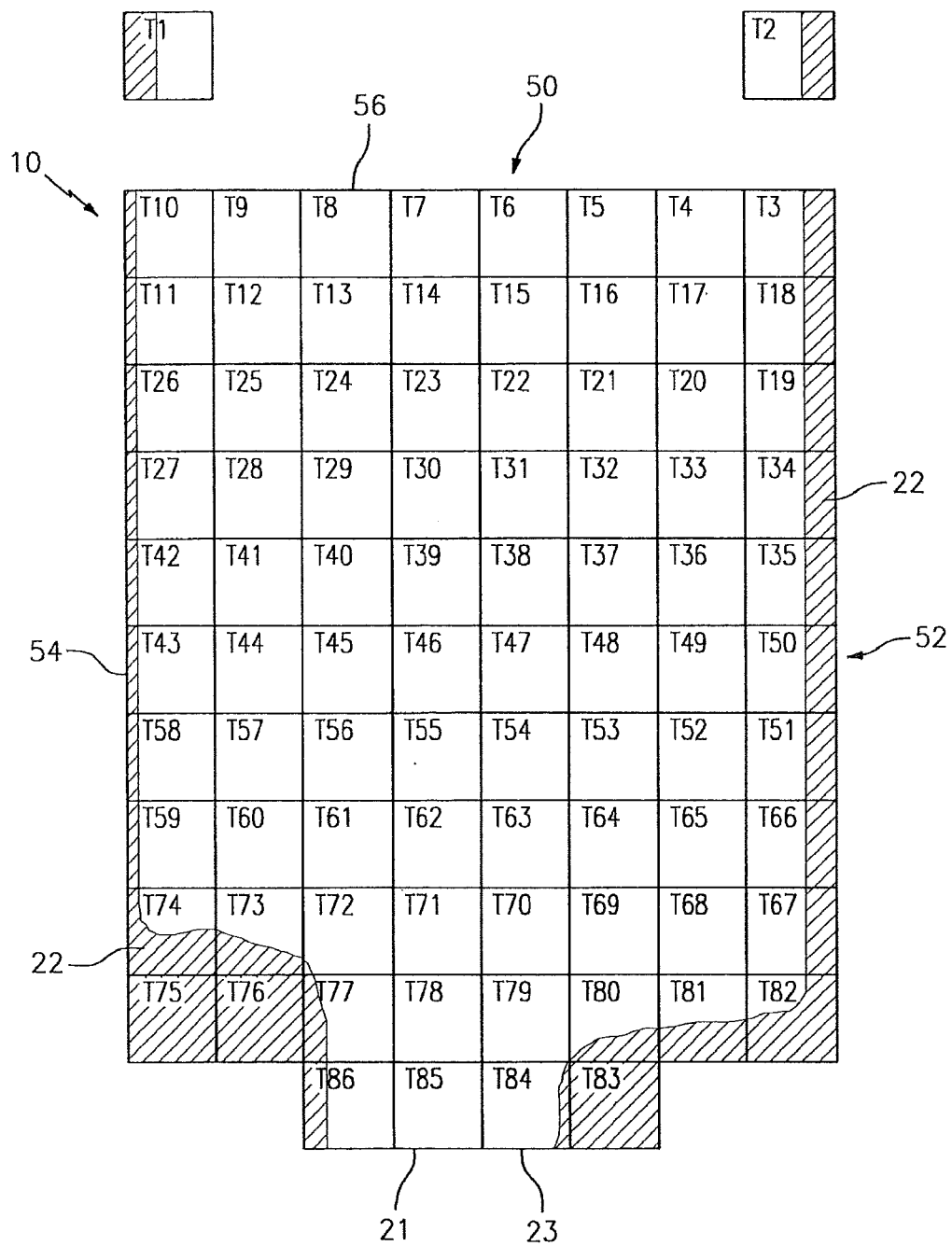
FIG. 6 is a diagrammatic illustration of a mapped analysis chamber.
Figure 7:
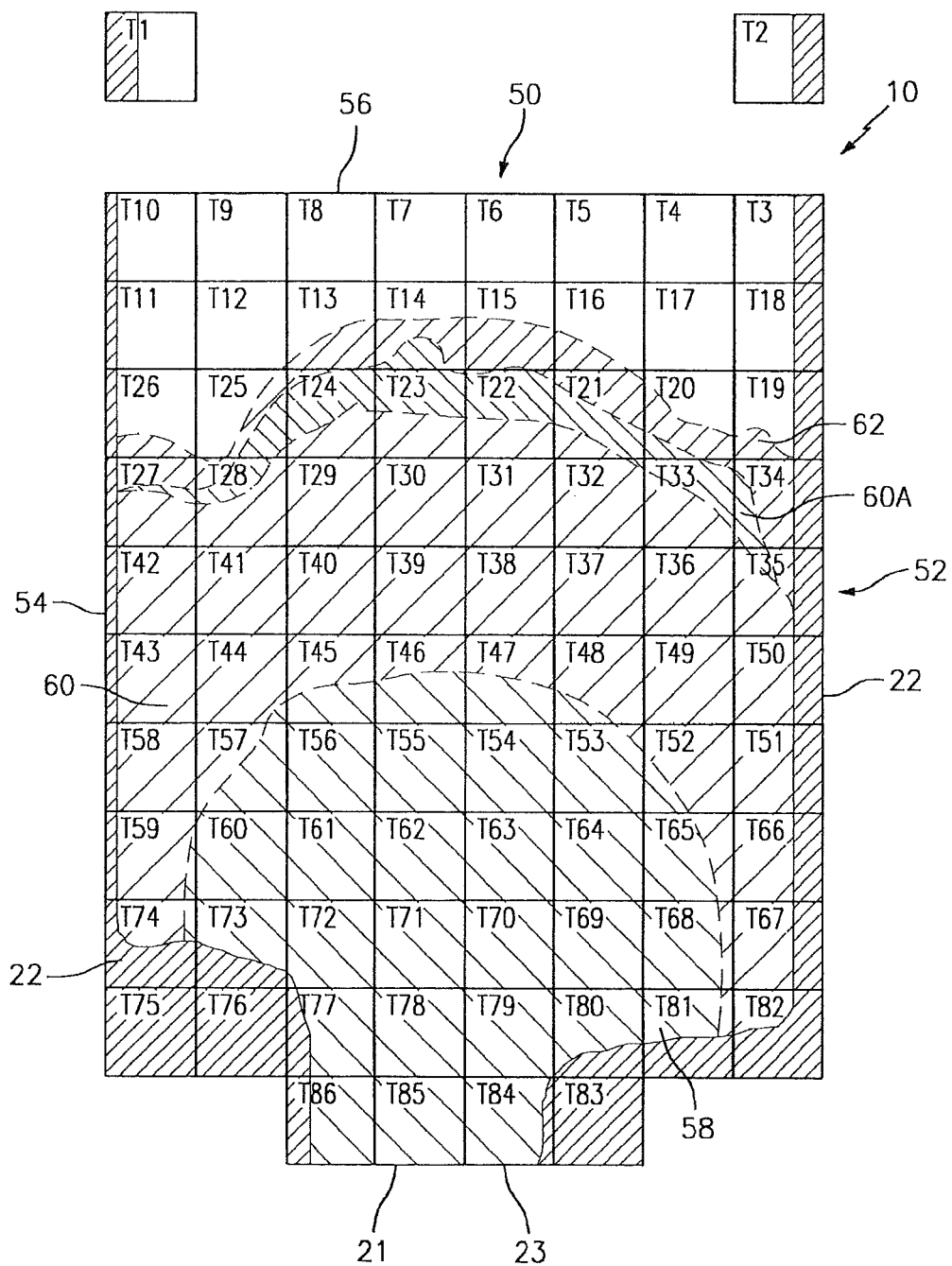
FIG. 7 is a diagrammatic illustration of a mapped analysis chamber, including a repeatable, predetermined distribution of sample constituents disposed within the sample chamber.
Figure 8:
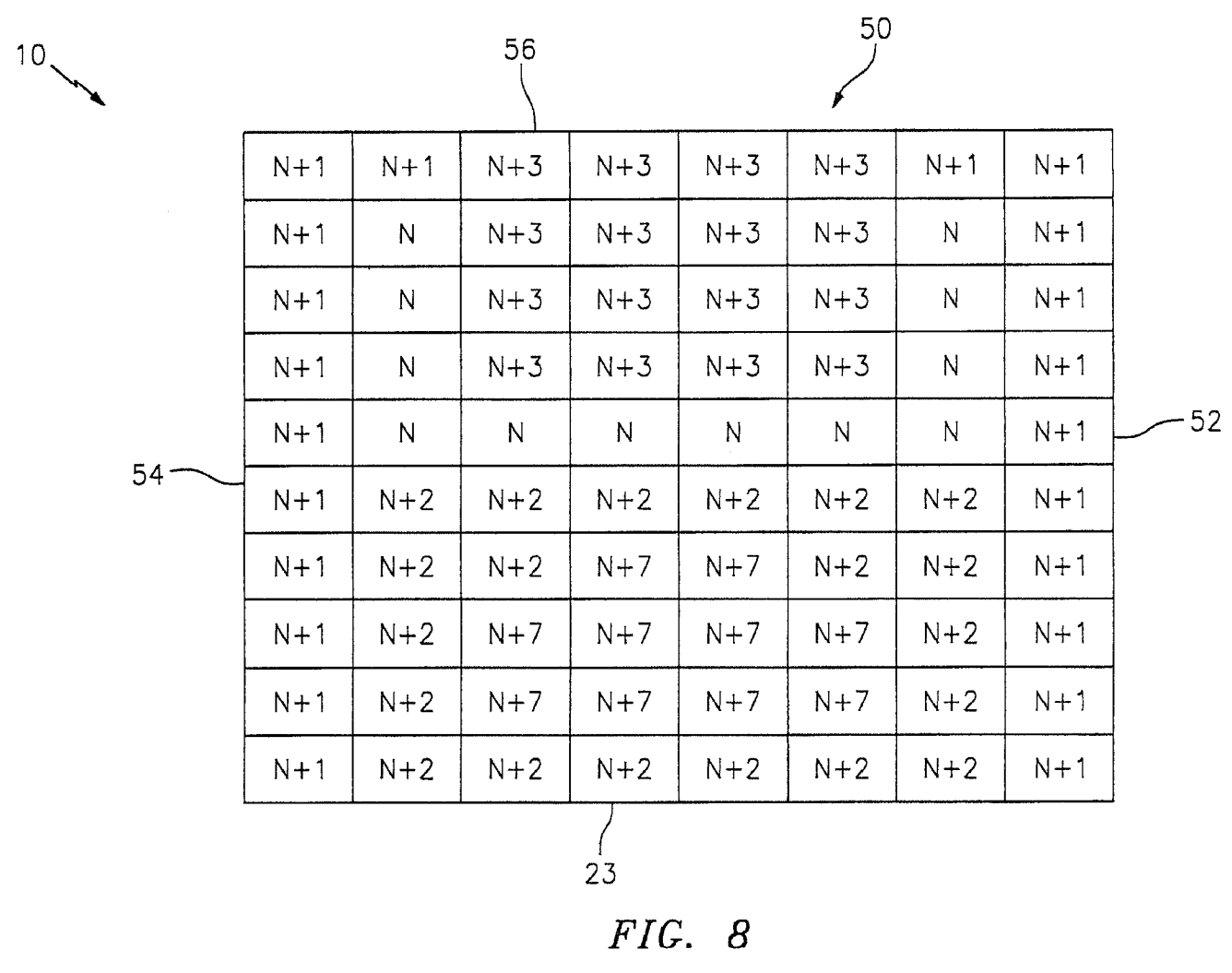

Now referring to FIGS. 6-8, an automated image analysis of biological fluid sample may include using a variety of imaging techniques, each designed to gather image data that permits identification and analysis of specific constituents within the sample. Using a whole blood sample as an example, an automated analysis device will preferably be operable to produce information relating to each of the constituents within the sample; e.g., RBC indices, WBC count, WBC differential, platelet enumeration, reticulocyte enumeration, etc. To acquire the desired image information, the analysis device may image the sample using several different imaging techniques; e.g., imaging the sample at multiple different wavelengths of light (e.g., using an epi-fluorescence light source and/or a transmission light source at different wavelengths); imaging the sample at different resolutions; imaging at different focal positions, etc.

The following patents and patent applications describe analysis devices operable to use different imaging techniques for acquiring data that permits specific identification and analysis of constituents within the sample: U.S. patent application Ser. No. 13/204,415, entitled "Method and Apparatus for Automated Whole Blood Sample Analyses from Microscopy Images" (which is hereby incorporated by reference in its entirety) discloses methods for performing a WBC differential on a whole blood sample that include imaging a blood sample at a variety of different wavelengths, using an epi-fluorescence light source and a transmission light source; U.S. Pat. No. 8,472,693, entitled "Method and Apparatus for Determining at Least One Hemoglobin Related Parameter of a Whole Blood Sample" (which is hereby incorporated by reference in its entirety) discloses methods for determining RBC indices including RBC cell volume (CV), mean cell volume (MCV), cell hemoglobin concentration (CHC), mean cell hemoglobin concentration (MCHC), and mean cell hemoglobin content (MCH), as well as their population statistics, using transmission light sources; U.S. patent application Ser. No. 13/730,095, entitled "Method and Apparatus for Automated Platelet Identification Within a Whole Blood Sample From Microscopy Images" (which is hereby incorporated by reference in its entirety) discloses methods for identifying and enumerating platelets within a sample that utilizes epi-fluorescent light sources; and U.S. patent application Ser. No. 13/729,887, entitled "Method for Rapid Imaging of Biologic Fluid Samples" (which is hereby incorporated by reference in its entirety) discloses methods for analyzing a sample at high and low image resolutions, which resolutions may facilitate data acquisition.

For an automated analysis device 12, it is desirable to produce the desired information in a minimum amount of time. It is also desirable to produce the desired information using a minimal amount of image data, thereby reducing the image data handling and storage requirements of the device.

For at least these reasons, aspects of the present invention coordinate the performance of those imaging techniques used to identify and/or analyze specific constituents within the sample with the position of the constituents within the sample. In other words, imaging techniques used to identify and/or analyze a constituent within a sample are implemented only in areas of the sample where that specific constituent is likely to be present (e.g., where a statistically significant population of the constituent is likely to be present), and not in areas where that specific constituent is not likely to be present. This selective implementation of imaging techniques can be utilized in instances where multiple types of analyses of the sample are to be performed or in instances when only one or more select type of analysis is to be performed. The analysis device 12 is adapted perform the imaging techniques described below.

According to aspects of the present invention, the sample chamber 10 is mapped to provide locatable sub-regions within the sample chamber. The mapping is described herein after as an orthogonal map (e.g., an X-Y orthogonal) having tiles. The term "tiles" as used herein refers to sub-regions defined by the rows and columns of the map. The tiles are not limited to any particular geometry or size, and are not required to have four equal length sides. The chamber mapping is not limited to an orthogonal mapping. The tiles may represent individual image fields, and the collective image fields may capture all or substantially of the sample residing within the chamber 10. The tiles may be collectively assembly to form a single image of all, or substantially all, of the sample residing within the chamber 10.

FIG. 6 diagrammatically illustrates an orthogonal mapping 50 applied to an analysis chamber 10 that includes tiles numbered T1-T86. Tiles T1 and T2 are reference tiles separated from the chamber, and are used to produce a reference image for a glue line 22/air interface. Tiles T83-T86 are aligned with chamber regions located at the filling edge 23 of the chamber where the chamber inlet 21 resides. In the chamber embodiment shown in FIG. 6, tile T83 is aligned with a chamber region predominantly filled with a glue line 22, and tile T86 is aligned with a chamber partially filled with a glue line 22. Consequently, the chamber inlet 21 is disposed there between, aligned with tiles T84, T85, and a portion of T86. Tiles T3, T18, T19, T34, T35, T50, T51, T66, T67, and T82 are aligned with the right lateral edge 52 of the chamber 10, and the chamber region aligned with each tile is at least partially filled with a glue line that forms the right lateral boundary of the analysis chamber 10. Tiles T10, T11, T26, T27, T42, T43, T58, T59, T74, and T75 are aligned with the left lateral edge 54 of the chamber 10, and the chamber region aligned with each tile is at least partially filled with a glue line 22 that forms the left lateral boundary of the analysis chamber 10. Tiles T3-T10 are disposed along the edge 56 of the chamber 10 opposite the filling edge of the chamber 10.

In some applications, constituents within a sample residing within an analysis chamber 10 will assume a repeatable non-uniform distribution within the analysis chamber. The term "repeatable non-uniform distribution" is used to mean that when the same type of sample (e.g., undiluted whole blood) is disposed in a particular type of analysis chamber (e.g., the chamber described above as being defined by planar members; or a slide), certain constituents within the sample repeatably occupy particular regions within the chamber in a non-uniform distribution; i.e., not every chamber region occupied by the sample has the same type and/or number of constituents as the other chamber regions. FIG. 8 below provides an example of a repeatable non-uniform distribution of whole blood within an analysis chamber. Hence, a statistically significant number (e.g., a number adequate to perform an analysis) of certain constituents will be repeatably present in certain regions of the analysis chamber and not in other regions. A predetermined representative version of the repeatable non-uniform distribution can, for example, be determined by evaluating a meaningful number of samples of the same type disposed within the same chamber. It has been determined that in these instances, constituents within the sample will repeatably occupy certain regions within the chamber. The predetermined distribution may, therefore, be empirically based on the statistical positions of the constituents within a meaningful number of filled chambers. In these applications, the positions of the statistically significant numbers of constituents within the sample are known, and can be accessed without the need to perform an imaging step for the purpose of finding the locations of the aforesaid constituents within the image of the sample chamber.

For example, using the chamber 10 described above as an example, a whole blood sample may be drawn into the chamber inlet 21 along the filling edge 23 by capillary forces. As the sample is drawn into the chamber 10, the sample travels toward the opposite end 56 of the chamber 10, and laterally outward toward the glue lines 22 that form the lateral boundaries of the chamber 10. As the whole blood sample distributes within the chamber 10, constituents (e.g., WBCs, RBCs, platelets, plasma) distribute in a repeatable non-uniform pattern. Specifically in the aforesaid non-uniform distribution, a statistically significant number of the WBCs within the sample will travel a limited distance into the chamber 10 and will populate the chamber region 58 proximate the chamber inlet 21. In FIG. 7, the chamber region 58 that will repeatably contain a statistically significant number of the WBCs within the sample is aligned with tiles T53-T56, T60-T64, T69-T72, and T78-T79, and portions of T68, T65, T52, T48-T45, T57, and T73.

A statistically significant portion of the RBCs within the sample will also travel a distance into the chamber 10, but will travel further into the chamber 10 than the WBCs. The RBCs will thereby populate a chamber region 60 contiguous with, but a distance further away from the chamber inlet 21 than the chamber region 58 populated by the statistically significant number of WBCs. In FIG. 7, the chamber region 60 that will repeatably contain a statistically significant number of the RBCs within the sample is aligned with tiles T22, T23, T27-T33, T42-T36, T43, T58, and T49, and portions of T65, T52, T59, T25, T24, T21, and T20. The disparity in travel distance is at least in part attributable to the height of the analysis chamber (e.g., a 4 micron separation between the interior surfaces of the planar members 14, 16 that form the chamber 10), and the relative sizes of WBCs vs. RBCs. WBCs are on average substantially larger in size than RBCs, and their travel within the chamber may therefore be impeded by frictional contact with the interior surfaces of the planar members 14, 16. RBCs in their normal state will typically not contact both interior surfaces of the planar members 14, 16. Plasma and platelets are distributed throughout the chamber by capillary flow.

Analyses directed specifically to plasma may be performed in the chamber regions beyond where the statistically significant portions of RBCs are located, which regions are relatively free of WBCs and RBCs and consequently predominated by plasma. In FIG. 7, the chamber regions that will repeatably be predominated by plasma within the sample are shown as region 62, which region is aligned with portions of tiles T13-16, T19-T21, and T25-T27. Note that region 62 is arbitrarily shown here for description purposes, and regions predominated by plasma may also be found elsewhere. As a result of their substantially smaller relative size, platelets can be imaged throughout the chamber.

The above described repeatable alignment of chamber regions containing certain constituents within the sample and particular tiles is provided as a non-limiting example, and alternative tile/constituent alignments may be used; e.g., the aforesaid alignment may be influenced by the height of the chamber and/or the volume of the sample introduced into the chamber.

The repeatable non-uniform distribution of constituents within the sample can also be at least in part attributable to reagents disposed within the chamber. For example, in some analyses of whole blood samples it is desirable to subject at least a portion of the RBCs within the sample to an isovolumetric sphering agent; e.g., See U.S. Pat. No. 8,472,693 incorporated by reference above. In some applications, the isovolumetric sphering agent may be disposed within the chamber prior to sample entering the chamber in a manner that not all of the RBCs will be subjected to the sphering agent. As a result, and as shown in FIG. 7, the leading edge (i.e., the edge of the region furthest from the chamber inlet—depicted as region 60A) of the chamber region 60 containing the statistically significant numbers of RBCs will contain a substantial number of sphered RBCs, and the remainder of the region 60 containing the statistically significant numbers of RBCs will not contain a substantial number of sphered RBCs. The sphered RBCs are particularly useful for certain types of RBC analyses.

As indicated above, the above described repeatable non-uniform distribution of sample constituents is provided as a non-limiting example of distribution within a specific chamber embodiment. In alternative embodiments (e.g., a smear on a slide), a non-uniform distribution may assume a completely different configuration. Regardless of the particular repeatable non-uniform distribution, according to aspects of the present invention a mapping may be applied to the chamber that allows coordination of the performance of those imaging techniques used to identify and/or analyze specific constituents within the sample with the position of statistically sufficient numbers of the particular constituents within the sample. In other words, imaging techniques used to identify and/or analyze a constituent within a sample are implemented only in areas of the sample where that specific constituent is likely to be present (e.g., where a statistically significant population of the constituent is likely to be present, and/or favorably imaged), and not in areas where that specific constituent is not likely to be present (or cannot be favorably imaged).

Using the determined, repeatable non-uniform distribution, the respective image analyses of particular constituents within the sample can be performed in an efficient manner in terms of time and data volume. For example, if the analysis device is commanded to perform a WBC analysis, only those mapping tiles aligned with the sample regions containing a statistically significant population of WBCs are imaged using the imaging techniques required to perform the requested analysis. Similarly, if the analysis device is commanded to perform a RBC analysis, only those mapping tiles aligned with the sample regions containing a statistically significant population of RBCs are imaged using the imaging techniques required to perform the requested analysis. As indicated above, certain RBC analyses are best performed on sphered RBCs. In those instances, only those mapping tiles aligned with the sample regions containing a statistically significant population of sphered RBCs are imaged using the imaging techniques required to perform the requested analysis. The same approach can be used for plasma analyses, etc.

FIG. 8 shows a diagrammatic depiction of a sample chamber with numeric values (e.g., N to N+7, where "N" is an integer) representative of the number of images necessary for multiple analyses of a whole blood sample; e.g., WBC analyses, platelet analyses, RBC analyses, plasma analyses, etc. In the depiction, the number of images necessary to be taken for all the analyses varies as a function of the position of the tile, and therefore the aligned region of the sample to be imaged at that position. Within the mapping, a group of tiles centrally located but also located closer to the chamber inlet indicate that a total of "N+7" images are to be taken for each of those tiles. That number of images represents the total number of images per tile necessary for the analyses of the WBCs, which tiles (per the repeatable non-uniform distribution of constituents within the sample) are aligned with a statistically sufficient number of WBCs in the sample. To illustrate further, within the mapping a group of tiles centrally located but also located further away from the chamber inlet indicate that a total of "N+3" images are to be taken for each of those tiles. That number of images represents the total number of images per tile necessary for the analyses of the sphered RBCs, which tiles (per the repeatable non-uniform distribution of constituents within the sample) are aligned with a statistically sufficient number of sphered RBCs in the sample. It should be noted that the imaged regions (i.e., tiles) for any particular constituents are often increased beyond what the known repeatable non-uniform distribution of constituents within the sample indicates to ensure that sufficient data is collected. The increased number of tiles also accounts for statistical variations and for variations in volumetric fill of the chamber.

It can be seen from the diagrammatic illustration that the total number of images for the eighty (80) tiles shown equals eighty times "N" (80*N), plus an additional one hundred and eighty (180) images. If "N+7" images were taken of all eighty tiles, it would equal 80*N images plus an additional five hundred and sixty (560) images, which represents a different of three hundred and eighty (380) images, each of which images adds significantly to the total analysis time and image storage and handling requirements.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A method for imaging a biologic fluid sample having one or more constituents, which sample is quiescently disposed within an analysis chamber, comprising:
providing a spatial mapping of the analysis chamber, which spatial mapping defines a plurality of sub-regions of the analysis chamber;
providing a predetermined repeatable non-uniform spatial distribution of at least one of the one or more constituents within the sample relative to the chamber, wherein the distribution indicates a probability that the at least one of the one or more constituents within the sample resides in particular sub-regions of the analysis chamber;
selecting at least one imaging method for imaging one or more of the analysis chamber sub-regions based on the probability as indicated by the distribution; and
creating image data representative of the biologic fluid sample in select chamber sub-regions, using the at least one imaging method selected for the respective one or more of the select chamber sub-regions.

2. The method of claim 1, wherein the biologic fluid sample is blood and the constituents include at least one of white blood cells, red blood cells, plasma, or sphered red blood cells.

3. The method of claim 1, wherein the chamber is a microscope slide.

4. The method of claim 1, wherein the step of creating image data representative of the biologic fluid sample in select chamber sub-regions includes creating image data representative of the biologic fluid sample in all chamber sub-regions.

5. The method of claim 1, wherein the predetermined repeatable non-uniform spatial distribution of one or more constituents within the sample disposed within the chamber indicates a plurality of sub-regions where a number of white blood cells reside within the chamber.

6. The method of claim 1, wherein the predetermined repeatable non-uniform spatial distribution of one or more constituents within the sample disposed within the chamber indicates a plurality of sub-regions where a number of red blood cells reside within the chamber.

7. The method of claim 1, further comprising analyzing the biologic fluid sample, using the image data representative of the biologic fluid sample in the select chamber sub-regions.

8. The method of claim 1, wherein the probability that the at least one of the one or more constituents within the sample resides in particular sub-regions of the analysis chamber is based on empirical data.

9. An apparatus for imaging a biologic fluid sample, comprising:
a chamber operable to quiescently hold the biologic fluid sample, which chamber is spatially mapped to divide the chamber into a plurality of sub-regions;
a sample illuminator;
at least one image dissector operable to produce image signals representative of the sample residing within the chamber; and
a processor in communication with the sample illuminator, the at least one image dissector, and a non-transitory memory storing instructions, which instructions include a predetermined repeatable non-uniform spatial distribution of one or more constituents within the fluid sample quiescently disposed within the chamber, wherein the spatial distribution indicates a probability that the at least one of the one or more constituents within the sample resides in particular sub-regions of the analysis chamber, and when executed the instructions cause the processor to:
select at least one imaging method for imaging one or more of the analysis chamber sub-region based on the probability as indicated by the distribution;
control the sample illuminator and the image dissector to create image data representative of the biologic fluid sample in select chamber sub-regions, using the at least one imaging method selected for the respective one or more of the select chamber sub-regions.

10. The apparatus of claim 9, wherein the chamber is a microscope slide.

11. The apparatus of claim 9, wherein the predetermined repeatable non-uniform spatial distribution of one or more constituents within the sample disposed within the chamber indicates a plurality of sub-regions where the number of white blood cells reside within the chamber.

12. The apparatus of claim 9, wherein the predetermined repeatable non-uniform spatial distribution of one or more constituents within the sample disposed within the chamber indicates a plurality of sub-regions where a number of red blood cells reside within the chamber.

13. The apparatus of claim 9, wherein the number of at least one of the constituents within the sample in each sub-region of the chamber is based on empirical data.

14. An apparatus for imaging a biologic fluid sample, comprising:
a chamber operable to quiescently hold the biologic fluid sample;
a sample illuminator;
at least one image dissector operable to produce image signals representative of the sample residing within the chamber; and
a processor in communication with the sample illuminator, the at least one image dissector, and a non-transitory memory storing instructions, which instructions include a predetermined repeatable non-uniform spatial distribution of one or more constituents within the fluid sample quiescently disposed within the chamber, wherein the spatial distribution indicates a probability that the at least one of the one or more constituents within the sample resides in particular sub-regions of the analysis chamber, and when executed the instructions cause the processor to:
apply a spatial map to the analysis chamber that defines the chamber sub-regions;
select at least one imaging method for imaging one or more of the analysis chamber sub-regions based on the probability as indicated by the distribution;
control the sample illuminator and the image dissector to create image data representative of the biologic fluid sample in select chamber sub-regions, using the at least one imaging method selected for the respective one or more of the select chamber sub-regions.

15. The apparatus of claim 14, wherein the chamber is a microscope slide.

16. The apparatus of claim 14, wherein the predetermined repeatable non-uniform spatial distribution of one or more constituents within the sample disposed within the chamber indicates a plurality of sub-regions where the number of white blood cells reside within the chamber.

17. The apparatus of claim 14, wherein the predetermined repeatable non-uniform spatial distribution of one or more constituents within the sample disposed within the chamber indicates a plurality of sub-regions where a number of red blood cells reside within the chamber.

18. The apparatus of claim 14, wherein the number of at least one of the constituents within the sample in each sub-region of the chamber is based on empirical data.

* * * * *